United States Patent [19]

Richards et al.

[11] 4,184,752

[45] Jan. 22, 1980

[54] INSTRUMENT ILLUMINATOR

[75] Inventors: William Richards, Medway; Bernard Grolman, Worcester, both of Mass.

[73] Assignee: American Optical Corporation, Southbridge, Mass.

[21] Appl. No.: 894,226

[22] Filed: Apr. 7, 1978

[51] Int. Cl.² .......................... A61B 3/10; A61B 3/14; G03B 29/00

[52] U.S. Cl. ..................................... 351/16; 354/62; 351/7

[58] Field of Search ................... 354/62; 351/16, 6, 7, 351/9–12; 362/11, 12, 13

[56] References Cited
U.S. PATENT DOCUMENTS

| | | | |
|---|---|---|---|
| 2,482,430 | 9/1949 | Noel | 362/12 |
| 3,915,564 | 10/1975 | Urban | 351/7 |
| 4,023,189 | 3/1974 | Govignon | 354/62 |

Primary Examiner—John K. Corbin
Assistant Examiner—Rodney B. Bovernick
Attorney, Agent, or Firm—Jeremiah J. Duggan; Alan H. Spencer; Stephen A. Schneeberger

[57] ABSTRACT

An illuminator including an incandescent lamp and strobe tube in a pivotable carrier adapted to selectively alternately position the lamp and tube in an identical single position of use, each being electrically activable only when at the position of use. The incandescent lamp affords continuous light of relatively low intensity for illumination of objects to be examined and the strobe tube affords short duration high intensity flash illumination for photographic recording purposes.

3 Claims, 5 Drawing Figures

INSTRUMENT ILLUMINATOR

BACKGROUND OF THE INVENTION

1. Field of the Invention

This invention relates to instrument illuminators and more particularly to an illuminator for an ophthalmic examining and photographic recording instrument.

2. Description of the Prior Art

Ophthalmological instruments include investigatory tools such as the ophthalmoscope or slit lamp which may be used to view the interior and/or other parts of the eye for detection and identification of vascular system disorders and/or a variety of other anomalies.

The recording of fundus disorders or other eye conditions of interest however has heretofore required the use of photographic equipment possessing little or no utility as an investigatory tool. Lacking is the advantage of being able to simply and efficiently photographically record a condition of interest at any time during routine examination without otherwise interrupting the examination procedure.

Drawbacks of prior art attemps to render examining or recording instruments dual functioning, as in the case of U.S. Pat. No. 4,023,189 for example, are ungainliness of equipment, undue complexity of operation and less than optimum efficiency particularly with respect to illuminating areas under examination for photographing points of interest needing subsequent study of original visual findings.

In addition to the aforesaid and other obvious inadequacies inefficiencies and ungainlinesses of devices employing arc lamps and the like, as in U.S. Pat. No. 4,023,189, the more recent use of strobe tubes for high intensity photographic illumination has been hampered by the need for movable mirrors and/or fixed beam splitters to selectively alternately direct low intensity examining the high intensity strobe light along a common instrument axis. Mirrors require exacting alignment when in use and complex sliding or tilting systems for moving them into and away from positions of use. Beam splitters on the other hand, have the well known disadvantage of loosing approximately one half of light intended for transmission or reflection. Light directed upon a beam splitter for transmission becomes partially reflected and vice versa.

In view of the foregoing, it is a principal object of this invention to provide an illuminator of improved, simple and efficient design for use in examining and recording instruments.

Another object is to provide an illuminator for rendering an investigatory instrument adaptable to photographic recording use with minimal cost, incumberance and/or need for alteration of the original form of the instrument.

Still another object of the invention is to provide in simple, compact and efficient fashion, means for incorporating dual light sources in an ophthalmic instrument system which source may be selectively alternately positioned at a light emitting station in the system and energized thereat, one light source supplying short duration high intensity illumination for photographic recording purposes and the other supplying relative low intensity continuous illumination of ophthalmic screening.

Other objects and advantages of the invention will become apparent from the following description.

SUMMARY OF THE INVENTION

The aforesaid objects and their corollaries are accomplished by the provision of an illuminator having a tiltable lamp holder carrying a pair of light sources one in the form of an incandescent lamp and the other a strobe tube. The principal light-emitting points of the light sources are located equally radially distant from an axis of pivot means about which the holder is adapted to be tilted. A base supports the lamp holder and in turn, is adapted to be fixed within the system of an instrument intended to receive the illuminator.

At one position of the lamp holder on the supporting base, the principal light-emitting point of one light source is aligned with a given illuminating axis, e.g. an optical axis of an instrument fitted with the illuminator. Tilting the holder to a second position moves the one light source away from the illuminating axis and brings the other light source into similar alignment therewith. Stop means establishes precision alignment of the respective light-emitting points upon the single illuminating axis and electrical contacts are provided for affecting appropriate electrical activation and deactivation of the light sources.

By selectively bringing the incandescent lamp into alignment with an instrument's illuminating axis, the instrument may be utilized as an investigatory tool. By bringing the strobe lamp into alignment with the instrument's illuminating axis, high intensity strobe (flash) illumination may be provided along the axis for photographic use.

Details of the invention will become more readily apparent from the following description when taken in conjunction with the accompanying drawings.

IN THE DRAWINGS

DESCRIPTION OF THE PREFERRED EMBODIMENTS

Figure 1:
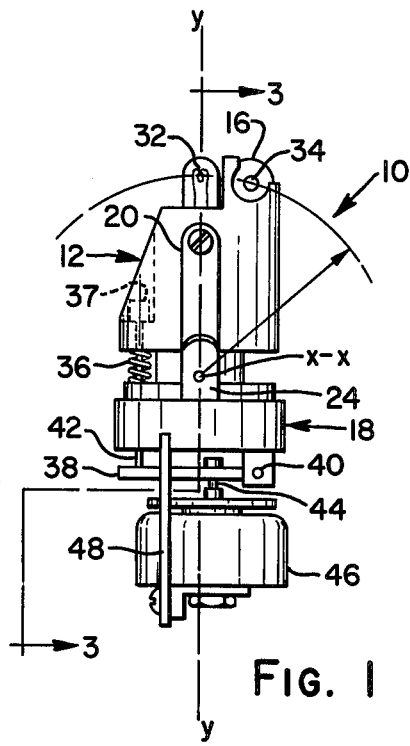
FIG. 1 is a slide elevational view of a preferred embodiment of the invention.

In the illustrated form of the invention, illuminator 10 (FIGS. 1-3) comprises lamp holder 12 within which is supported an incandescent lamp 14 and strobe lamp 16. Lamp 16 will be referred to hereinafter as flash tube 16, its function being typically that of emitting a high intensity flash of light suitable for flash photography when electrically triggered as will be subsequently described in detail.

Incandescent lamp 14, being intended to provide continuous light of lower intensity than tube 16 but preferably sufficient for intraocular examination, may comprise a halogen lamp.

Lamp holder 12 is preferably formed of an electrical insulating material and is pivotally mounted upon a supporting base 18 by means of depending leaves 20 having pivot pins 22 (FIG. 3) which extend respectively through one of each of a pair of parallel receiving blades 24.

Support 26 for lamp 14, having pivot pins 28, is similarly mounted by blades 30 within platform 18. Leaves 20 and blades 24 and 30 are preferably formed of metal and may be used as electrical conductors for energizing lamps 14 and 16. All pivot pins 22 and 28, are aligned on axis x—x thereby rendering holder 12 pivotable about axis x—x.

Figure 4:
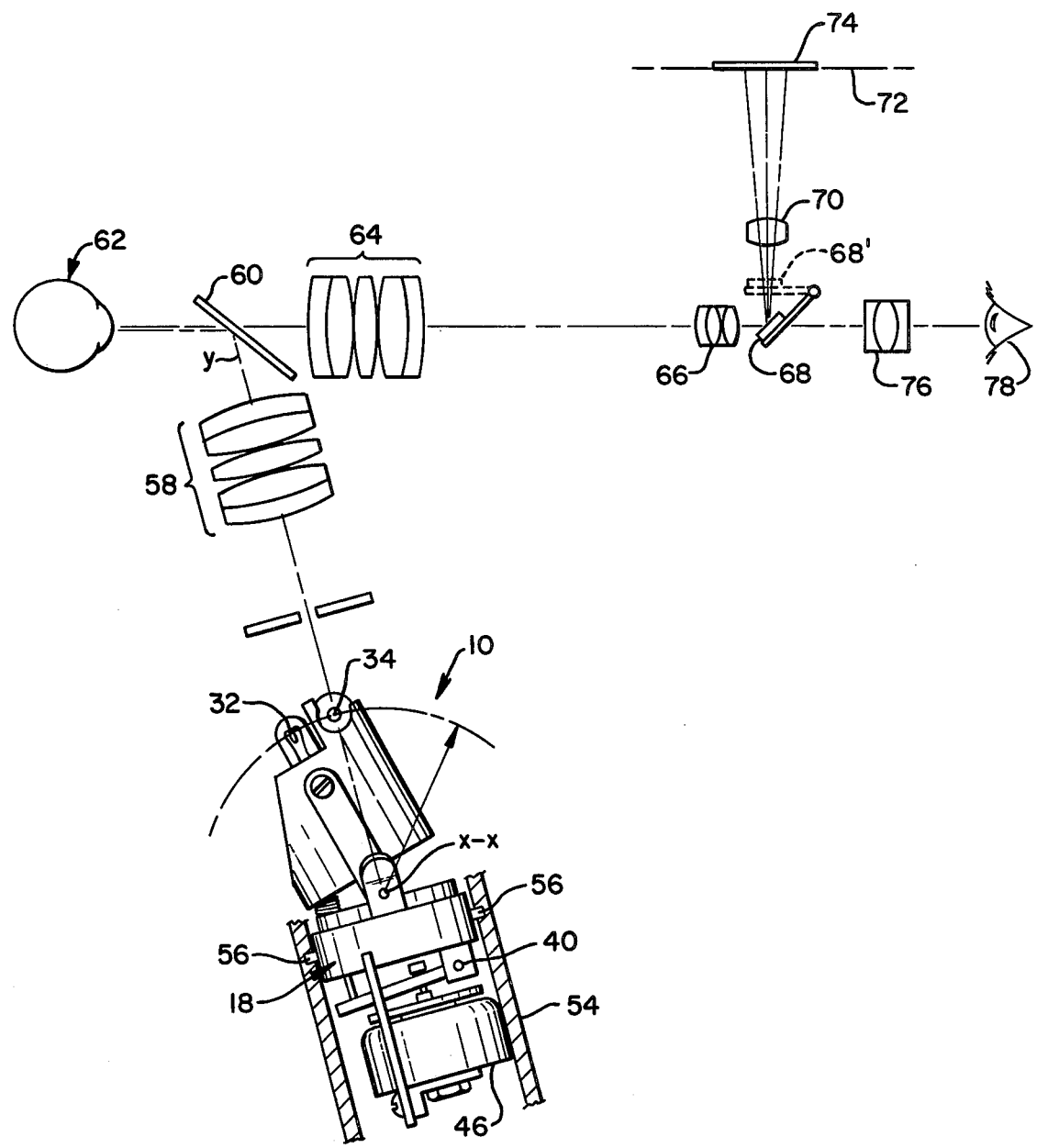
FIG. 4 is a diagrammatic illustration of a form of eye screening and photographing system to which the present invention has application, the illuminator of FIGS. 1-3 being illustrated in a position of use in the system.

Lamp 14 and tube 16, having their principal light-emitting points 32 and 34 (FIG. 1) equally-radially spaced from axis x—x, may be selectively alternately brought into coincidence with a single preselected point on axis y—y simply by pivoting holder 12 about axis x—x, i.e. from the position in FIG. 1 to that shown in FIG. 4. By "principal light-emitting points" it is meant, for example, the filament of incandescent lamp 14 and horizontal axis of the exposed portion of flash tube 16.

Spring 36 (FIGS. 1 and 2) biases holder 12 against stop 37 to the position illustrated in FIG. 1, i.e. with lamp 14 aligned with axis y—y, but yields to the tilting of holder 12 with actuation of tilting lever 38. Lever 38, being distally pivoted to base 18 by pin 40 (FIGS. 1 and 4) and proximally linked to holder 12 by wire 42 is actuated by rod 44 of solenoid 46. Bracket 48 fastened to base 18 supports solenoid 46.

Figure 2:
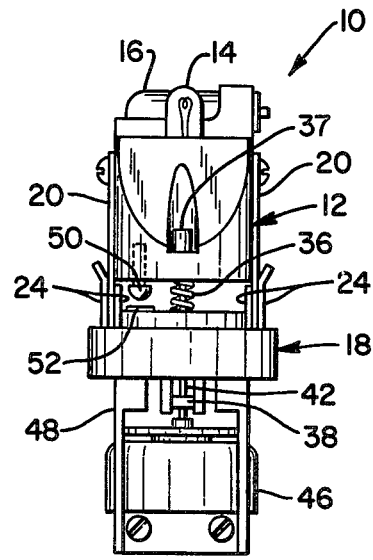
FIG. 2 is a front view of the illuminator of FIG. 1.
Figure 3:
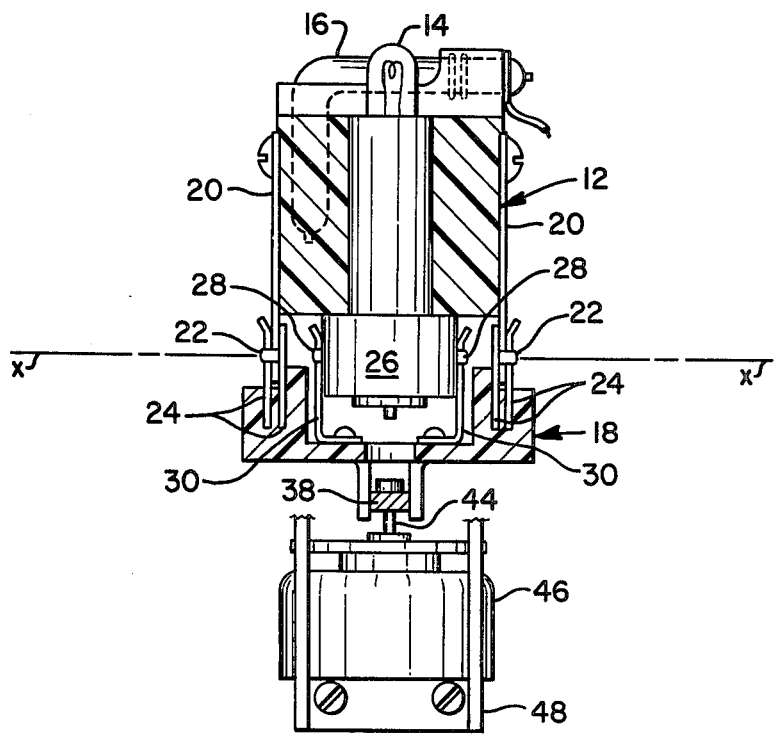
FIG. 3 is an enlarged cross-sectional view taken generally along lines 3—3 of FIG. 1.

The tilting of holder 12 from the position illustrated in FIG. 1 to that of FIG. 4 is accomplished by activation of solenoid 46 which moves rod 44, lever 38 and wire 42 downwardly until stop pin 50 engages stop 52 (FIG. 2). Stop pin 50 is adjustable in its effective length to the extent necessary to establish alignment of point 34 of tube 16 with y—y as illustrated in FIG. 4. Stop pin 50 and stop 52 provide the added function of an electrical switch to be described in detail hereinafter.

The exemplary instrument system of FIG. 4 comprises a support 54 for illuminator 10 to which base 18 may be fixed, e.g. with pins 56. This support may, for example, embody the handle of a hand-held ophthalmic instrument such as an ophthalmoscope fitted with a camera and having lens and mirror optical components of general type and arrangement illustrated. The system at FIG. 4 is but one of several forms of ophthalmic and other instrumentations to which illuminator 10 may be adapted.

In addition to illumination 10, the illustrated instrument components of FIG. 4 include a first multiple lens component 58 for receiving and directing light from illuminator 10 along axis y—y to beam splitter 60 for reflection into eye 62 under examination. Portions of this light reflected from within the eye, e.g. by its fundus, and passing through beam splitter 60 are imaged by objective 64 forwardly thereof. The image is erected by lenses 66 and reflected by mirror 68 through lens 70 into focus upon film plane 72 for photographic recording on film 74.

With mirror 68 selectively moved to the position illustrated by broken lines 68', the image erected by lenses 66 may be viewed with eyepice 76. At the same time, mirror 68 may be employed to provide a closure for the camera aperture (not shown) to protect film 74 from unwanted exposure. With the instrument system so placed in an eye-examining mode where a practitioner's eye 78 may view images of patient's eye 62, e.g. its fundus, for screening purposes, lamp holder 12 is pivoted back to the position illustrated in FIG. 1 so that light emitting point 32 of incandescent lamp 14 is aligned with axis y—y to afford constant illumination of the eye 62. Operation of illuminator 10 in the system of FIG. 4 may be accomplished as schematically illustrated in FIG. 5, it being understood that beyond the details of illuminator 10 per se the illustrations of FIGS. 4 and 5 merely exemplify the applicability of illuminator 10 and its adaptability to diagnostic instruments in general.

Figure 5:
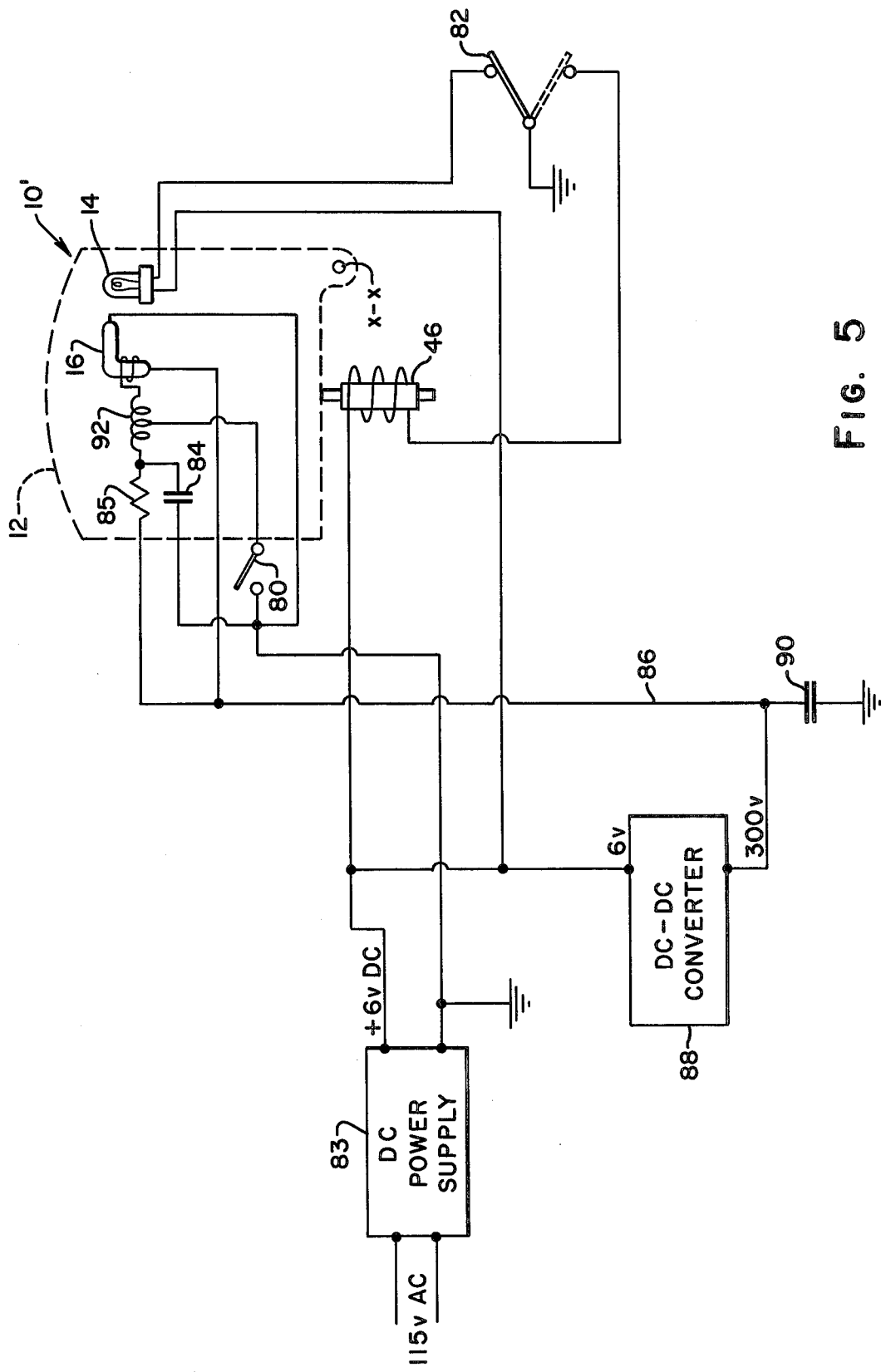
FIG. 5 is a schematic illustration of a system for electro-mechanically operating the illuminator.

In FIG. 5 wherein like reference numerals designate like parts of the embodiment of FIGS. 1-4, illuminator 10 is illustrated by broken lines 10' within which incandescent lamp 14 and flash tube 16 are supported for pivoting as a unit about axis x—x when solenoid 46 is activated.

Switch 80 represents an electrical switching connection made by pin 50 and stop 52 of FIG. 2. When lamp holder 12 is in the position illustrated in FIGS. 1-3, pin 50 and stop 52 are spaced apart so that switch 80 is open. When lamp holder is pivoted about axis x—x to the position illustrated in FIG. 4 by actuation of solenoid 46, pin 50 engages stop 52 and switch 80 becomes closed.

Manually operable switch 82 (FIG. 5) is used to control the operation of illuminator 10 wherewith it may be selectively switched from the above-described eye examing mode using incandescent lamp 14 to the flash photographing mode depicted in FIG. 4 using flash tube 16.

With switch 82 in the position of its full line illustration in FIG. 5, incandescent lamp 14 is energized from the DC power supply 83, e.g. of six volts. Simultaneously, trigger capacitor 84 (e.g. 0.22 mf) is charged through resistor 85 (e.g. 3.3 megohms) in circuit with high voltage line 86 carrying, for example, 300 volts from DC to DC converter 88. Flash capacitor 90 for tube 17 (e.g. 800 mf) is similarly simultaneously charged.

Switch 82 may be moved to the position illustrated by broken lines when movement of flash tube 16 into coincidence with axis y—y (FIG. 4) and firing for flash photography is required. This disconnects lamp 14, energizes solenoid 46 which tilts lamp holder 12 and closes switch 80. The closing of switch 80 energizes trigger transformer 92, causing capacitor 84 to discharge through trigger coil 94 firing tube 16 for the desired flash illumination.

Return of switch 82 to the position illustrated with full lines deenergizes solenoid 46, opens switch 80 and reenergizes lamp 14 wherewith the above-described flash cycle may be repeated when desired.

Switch 82 may be mechanically or otherwise linked to mirror 68 (FIG. 4) to perform the previously mentioned positioning of mirror 68 according to the selected mode of operation of the system of FIG. 4.

Those skilled in the art will readily appreciate that there are various modifications and adaptations of the precise form of the invention here shown and described that may suit particular requirements. Accordingly, the foregoing illustration is not to be interpreted as restrictive of the invention beyond that necessitated by the following claims:

We claim:

1. In the system of an ophthalmological instrument having an illuminator, means for receiving and directing light from said illuminator along an optical axis onto selected portions of an eye under examination, means for forming images of said portions of said eye remotely therefrom for observation by an operator of said instrument and means for selectively photographing said portions of said eye, said illuminator comprising:
- a stationary base having a central axis;
- a lamp holder pivotally mounted on said base about an axis extending substantially right-angularly through said central axis;
- a pair of spaced lamps carried by said holder, the principal light-emitting points of said lamps being equally radially spaced from said pivotal axis of said holder and disposed in a plane intersecting said central axis;
- biasing means resiliently fixing said holder in a first position of rotation about said pivotal axis where the principal light-emitting point of a first of said lamps lies approximately on said central axis of said base;
- means for selectively pivotally moving said holder from said first position of rotation about said pivotal axis to a second rotated position for bringing the principal light-emitting point of the second of said pair of lamps into substantial coincidence with said central axis, said means for moving said holder being selectively releasable for permitting automatic return of said holder to said first position of rotation by said biasing means.

2. The illuminator according to claim 1 wherein said means for moving said lamp holder comprises a solenoid.

3. The ophthalmological instrument system according to claim 1 wherein said one of said pair of lamps is incandescent for use in forming said images to be observed by said operator and the other of said pair of lamps comprises a flash tube for use in photographing said selected portions of said eye.

* * * * *